United States Patent [19]
Weichert et al.

[11] Patent Number: 6,166,002
[45] Date of Patent: Dec. 26, 2000

[54] SUBSTITUTED PHENYLALKENOYLGUANIDINES, PROCESS FOR THEIR PREPARATION, AND THEIR USE IN MEDICAMENTS AND IN DIAGNOSTICS

[75] Inventors: Andreas Weichert, Egelsback; Alfons Enhsen, Büettelborn; Eugene Falk, Frankfurt; Hans-Willi Jansen, Niedernhausen; Werner Kramer, Mainz-Laubenheim; Jan-Robert Schwark, Kelheim; Hans Jochen Lang, Hofheim, all of Germany

[73] Assignee: Aventis Pharma Deutschland GmbH, Frankfurt, Germany

[21] Appl. No.: 09/422,146

[22] Filed: Oct. 20, 1999

[30] Foreign Application Priority Data

Oct. 28, 1998 [DE] Germany .......................... 198 49 722

[51] Int. Cl.[7] .............................. A61K 31/56; C07J 9/00; C07J 41/00
[52] U.S. Cl. .......................... 514/182; 514/171; 552/553; 552/554
[58] Field of Search ................................... 514/171, 182; 552/553, 554

[56] References Cited

FOREIGN PATENT DOCUMENTS 0 624 594  11/1994  European Pat. Off. .

*Primary Examiner*—Barbara Badio
*Attorney, Agent, or Firm*—Foley & Lardner

[57] ABSTRACT

Substituted phenylalkenoylguanidines, processes for their preparation, uses as medicaments or diagnostics, and medicaments containing them are described.

The invention relates to substituted phenylalkenoylguanidines and their pharmaceutically tolerable salts and physiologically functional derivatives of the formula

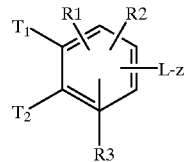

I in which the radicals have the meanings indicated, and their physiologically tolerable salts and processes for their preparation. The compounds are suitable as medicaments for the prophylaxis or treatment of gallstones.

20 Claims, No Drawings

SUBSTITUTED PHENYLALKENOYLGUANIDINES, PROCESS FOR THEIR PREPARATION, AND THEIR USE IN MEDICAMENTS AND IN DIAGNOSTICS

FIELD OF THE INVENTION

The invention relates to substituted phenylalkenoylguanidines and their pharmaceutically tolerable salts and physiologically functional derivatives.

BACKGROUND OF THE INVENTION

Apart from a number of factors, the formation of gallstones is essentially determined by the composition of the bile, in particular by the concentration and the proportion of cholesterol, phospholipids and bile salts. The prerequisite for the formation of cholesterol gallstones is the presence of bile which is supersaturated in cholesterol (see, for example, Carey, M. C. and Small, D. M. (1978) "The physical chemistry of cholesterol solubility in bile. Relationship to gallstone formation and dissolution in man," *J. Clin. Invest.* 61: 998–1026).

Up to now, gallstones mainly have been removed surgically. Thus, a great therapeutic need exists for medicinal gallstone dissolution and for the prevention of gallstone formation.

SUMMARY OF THE INVENTION

An object of the invention is to provide compounds that can prevent gallstone formation by preventing supersaturation of bile with cholesterol or by delaying the formation of cholesterol crystals from supersaturated bile. Other objects will be appreciated from the specification.

In one embodiment of the invention, there are provided compounds of formula I

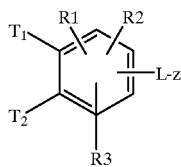

I wherein one of T1 and T2 is

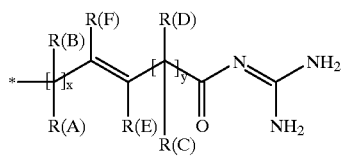

and the other one of T1 and T2 is hydrogen or each of T1 and T2 is

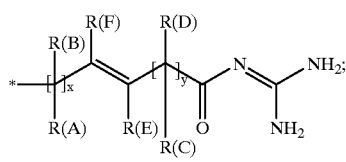

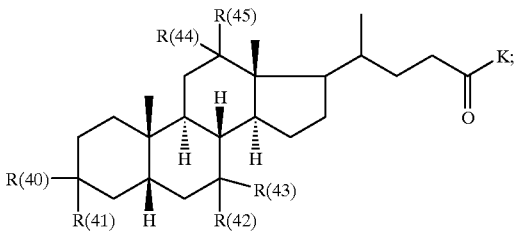

R(A), R(B), R(C), R(D) independently of one another are hydrogen, F, Cl, Br, I, CN, OH, $NH_2$, —$(C_1-C_8)$-alkyl, —O—$(C_1-C_8)$-alkyl, where each alkyl radical is unsubstituted or substituted one or more times by F; $(C_3-C_8)$-cycloalkyl, phenyl, benzyl, NHR(7), NR(7)R(8), O—$(C_3-C_6)$-alkenyl, O—$(C_3-C_8)$-cycloalkyl, O-phenyl, O-benzyl, where the phenyl nucleus is unsubstituted or substituted 1 to 3 times by F, Cl, $CF_3$, methyl, methoxy, NR(9)R(10);

R(7), R(8) independently of one another are hydrogen, —$(C_1-C_8)$-alkyl, where the alkyl radical is unsubstituted or substituted 1 to 3 times by F, $(C_3-C_8)$-cycloalkyl, $(C_3-C_6)$-alkenyl, $(C_3-C_8)$-cycloalkyl, phenyl, benzyl, where the phenyl nucleus is unsubstituted or substituted 1 to 3 times by F, Cl, $CF_3$, methyl, methoxy, NR(9)R(10); or R(7), R(8) together form a chain of 4 or 5 methylene groups, of which one $CH_2$ group is not replaced or replaced by oxygen, sulfur, NH, N—$CH_3$ or N-benzyl;

R(9), R(10) independently of one another are hydrogen, $(C_1-C_4)$-alkyl, $(C_1-C_4)$-perfluoroalkyl;

x is zero, 1 or 2;

y is zero, 1 or 2;

R(E), R(F) independently of one another are hydrogen, F, Cl, Br, I, CN, $(C_1-C_8)$-alkyl, O—$(C_1-C_8)$-alkyl, where the alkyl radical is unsubstitued or substituted 1 to 3 times by F, $(C_3-C_8)$-cycloalkyl, O—$(C_3-C_6)$-alkenyl, O-$(C_3-C_8)$-cycloalkyl, O-phenyl, O-benzyl, where the phenyl nucleus is unsubstituted or substituted 1 to 3 times by F, Cl, $CF_3$, methyl, methoxy, NR(9)R(10);

R(1), R(2), R(3) independently of one another are hydrogen, F, Cl, Br, I, CN, —$(C_1-C_8)$-alkyl, —O—$(C_1-C_8)$-alkyl, where each alkyl radical is unsubstituted or substituted one or more times by F, —(C=O)—N=C($NH_2$)$_2$, —($SO_{0-2}$)—$(C_1-C_8)$-alkyl, —($SO_2$)—NR(7)R(8), —O—$(C_0-C_8)$-alkylenephenyl, —$(C_0-C_8)$-alkylenephenyl, where the phenyl nuclei is unsubstituted or substituted 1 to 3 times by F, Cl, $CF_3$, methyl, methoxy, —$(C_0-C_8)$-alkylene-NR(9)R(10);

L is —O—, —NR(47)-, —$(C_1-C_8)$-alkylene-, —$(C_1-C_8)$-alkenylene-, —$(C_1-C_8)$-alkynylene-, —COO—, —CO—NR(47)-, —$SO_2$—NR(47)-, —O—$(CH_2)_n$—O—, —NR(47)-$(CH_2)_n$—O—, —NR(48)-CO—$(CH_2)_n$—O—, —CO—NR(48)-$(CH_2)_n$—O—, —O—CO—$(CH_2)_n$—O—, —$SO_2$—NR(48)-$(CH_2)_n$—O——NR(48)-CO—$CH_2$—$CH_2$—CO—NR(48)-$(CH_2)_n$—O—, —NR(48)-CO—CH=CH—CO—NR(48)-$(CH_2)_n$—O—, —NR(48)-$SO_2$—$(CH_2)_n$—O—;

R(47) is hydrogen, $(C_1-C_8)$-alkyl, R(48)-CO—, phenyl, benzyl;

R(48) is hydrogen, $(C_1-C_8)$-alkyl, phenyl and benzyl, where the phenyl nucleus is unsubstituted or substituted 1 to 3 times by F, Cl, $CF_3$, methyl, methoxy;

n is 1, 2, 3, 4, 5, 6, 7 or 8;

R(40) to R(45) independently of one another are hydrogen, —OR(50), —SR(50), NHR(50), —NR(50)$_2$, —O—(CO)—R(50), —S—(CO)—R(50), —NH—(CO)—R(50), —O—PO—(OR(50))-OR(50), —O—(SO$_2$)—OR(50), —R(50) and a bond to L; or R(40) and R(41), R(42) and R(43), R(44) and R(45) in each case together form the oxygen of a carbonyl group;

where always just one of the radicals R(40) to R(45) has the meaning of a bond to L;

K is —OR(50), —NHR(50), —NR(50)$_2$, —HN—CH$_2$—CH$_2$—CO$_2$H, —HN—CH$_2$—CH$_2$—SO$_3$H, —NH—CH$_2$—COOH, —N(CH$_3$)CH$_2$CO$_2$H, —HN—CH(R46)CO$_2$H, —OKa, where Ka is a cation, such as, for example, an alkali metal or alkaline earth metal ion or a quaternary ammonium ion;

R(46) is (C$_1$–C$_4$)-alkyl, benzyl, —CH$_2$—OH, H$_3$CSCH$_2$CH$_2$—, HO$_2$CCH$_2$—, HO$_2$CCH$_2$CH$_2$—;

R(50) is hydrogen, (C$_1$–C$_4$)-alkyl, phenyl or benzyl, where the phenyl nucleus is unsubstituted or substituted 1 to 3 times by F, Cl, CF$_3$, methyl, methoxy;

and their pharmaceutically tolerable salts and physiologically functional derivatives.

Other embodiments will be appreciated from the disclosure herein.

DETAILED DESCRIPTION OF THE PREFERRED EMBODIMENTS

Preferred compounds of formula I

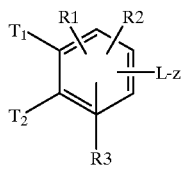

I are those in which one of T1 and T2 is

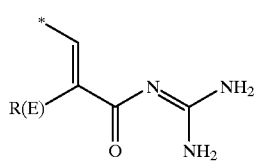

and the other one of T1 and T2 is hydrogen or each of T1 and T2 is

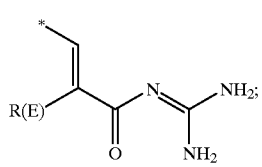

L-z is

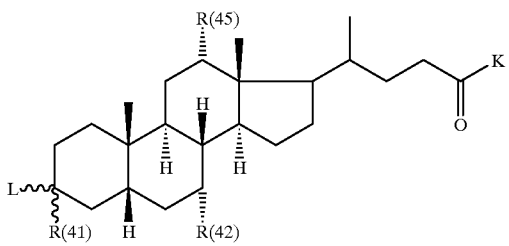

R(E) is hydrogen, F, Cl, CN, (C$_1$–C$_4$)-alkyl, —O—(C$_1$–C$_4$)-alkyl, where each alkyl radical is unsubstituted or substituted one or more times by F, (C$_3$–C$_6$)-cycloalkyl, (C$_3$–C$_8$)-alkenyl, O—(C$_3$–C$_6$)-cycloalkyl, O-phenyl, O-benzyl, where the phenyl nucleus is unsubstituted or substituted 1 to 3 times by F, Cl, CF$_3$, methyl, methoxy, NR(9)R(10);

R(9), R(10) independently of one another are hydrogen, CH$_3$, CF$_3$;

R(1), R(2), R(3) independently of one another are hydrogen, F, Cl, CN, —SO$_2$—(C$_1$–C$_4$)-alkyl, —SO$_2$—N((C$_1$–C$_4$)-alkyl)$_2$, —SO$_2$—NH(C$_1$–C$_4$)-alkyl, —SO$_2$—NH$_2$, —SO$_2$—(C$_1$–C$_4$)-alkyl, —(C$_1$–C$_4$)-alkyl, —O—(C$_1$–C$_4$)-alkyl, where each alkyl radical is unsubstituted or substituted one or more times by F, —O—(C$_0$–C$_4$)-alkylenephenyl, —(C$_0$–C$_4$)-alkylenephenyl, where each phenyl nucleus is unsubstituted or substituted 1 to 3 times by F, Cl, CF$_3$, methyl, methoxy;

L is —O—, —NR(47)-, —(C$_1$–C$_4$)-alkylene-, —(C$_1$–C$_4$)-alkenylene-, —(C$_1$–C$_4$)-alkynylene-, —COO—, —CO—NR(47)-, —SO$_2$—NR(47)-, —O—(CH$_2$)$_n$—O—, —NR(47)-(CH$_2$)$_n$—O—, —NR(48)-CO—(CH$_2$)$_n$—O—, —CO—NR(48)-(CH$_2$)$_n$—O—, —SO$_2$—NR(48)-(CH$_2$)$_n$—O—;

R(47) is hydrogen, (C$_1$–C$_4$)-alkyl, R(48)-CO—, phenyl, benzyl;

R(48) is hydrogen, (C$_1$–C$_4$)-alkyl, phenyl and benzyl, where the phenyl nucleus is unsubstituted or substituted 1 to 3 times by F, Cl, CF$_3$, methyl, methoxy;

n is 1–4;

R(41), R(42), R(45) independently of one another are hydrogen, —OR(50), NHR(50), —NR(50)$_2$, —O—(CO)—R(50), —NH—(CO)—R(50);

R(50) is hydrogen, (C$_1$–C$_4$)-alkyl, phenyl or benzyl, where the phenyl nucleus is unsubstituted or substituted 1 to 3 times by F, Cl, CF$_3$, methyl, methoxy;

K is —OR(50), —NHR(50), —NR(50)$_2$, —HN—CH$_2$—CH$_2$—CO$_2$H, —HN—CH$_2$—CH$_2$—SO$_3$H, —NH—CH$_2$—COOH, —N(CH$_3$)CH$_2$CO$_2$H, —OKa, where Ka is a cation, such as, for example, an alkali metal or alkaline earth metal ion or a quaternary ammonium ion;

and their pharmaceutically tolerable salts and physiologically functional derivatives.

Particularly preferred compounds of formula I

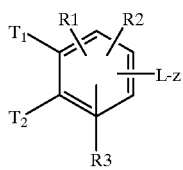

I are those in which
one of T1 and T2 is

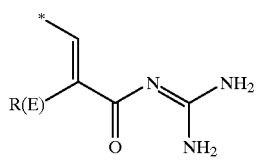

and the other one of T1 and T2 is hydrogen or each of T1 and T2 is

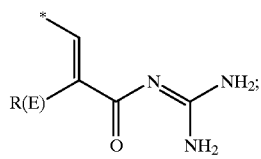

and L-z is

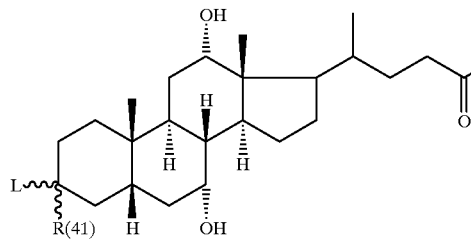

R(E) is hydrogen, F, Cl, CN, $(C_1-C_4)$-alkyl, $(C_1-C_4)$-alkyl, —O$(C_1-C_4)$-alkyl, $CF_3$, —$OCF_3$;

R(1), R(2) independently of one another are hydrogen, F, Cl, CN, —$SO_2$—$CH_3$, $SO_2NH_2$—, —$(C_1-C_4)$-alkyl, —O—$(C_1-C_4)$-alkyl, where each alkyl radical is unsubstituted or substituted one or more times by F; —O—$(C_0-C_4)$-alkylenephenyl, —$(C_0-C_4)$-alkylenephenyl, where each phenyl nucleus is unsubstituted or substituted 1 to 3 times by F, Cl, $CF_3$, methyl, methoxy;

R(3) is hydrogen;

L is —O—, —NR(47)-, —$CH_2$—$CH_2$—, CH═CH—, —(C≡C)—, —COO—, —CO—NR(47)-, —$SO_2$—NR(47)-, —O—$(CH_2)_n$—O—, —NR(47)-$(CH_2)_n$—O—, —NR(48)-CO—$(CH_2)_n$—O—, —CO—NR(48)-$(CH_2)_n$—O—, —$SO_2$—NR(48)-$(CH_2)_n$—O—;

R(47) is hydrogen, $(C_1-C_4)$-alkyl, R(48)-CO—, phenyl, benzyl;

R(48) is hydrogen, $(C_1-C_4)$-alkyl, phenyl and benzyl, where the phenyl nucleus is unsubstituted or substituted 1 to 3 times by F, Cl, $CF_3$, methyl, methoxy;

n is 1–4;

R(41) is hydrogen, —OH;

K is —OR(50), —NHR(50), —NR(50)$_2$, —HN—$CH_2$—$CH_2$—$CO_2H$, —HN—$CH_2$—$CH_2$—$SO_3H$, —NH—$CH_2$—COOH, —N($CH_3$)$CH_2CO_2H$, —OKa, where Ka is a cation, such as, for example, an alkali metal or alkaline earth metal ion or a quaternary ammonium ion;

R(50) is hydrogen, $(C_1-C_4)$-alkyl, phenyl or benzyl, where the phenyl nucleus is unsubstituted or substituted 1 to 3 times by F, Cl, $CF_3$, methyl, methoxy;

and their pharmaceutically tolerable salts.

Very particularly preferred compounds of the formula I are those having the structure Ia

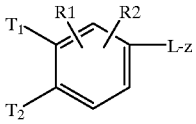

Ia in which
one of T1 and T2 is

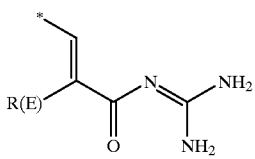

and the other one of T1 and T2 is hydrogen or each of T1 and T2 is

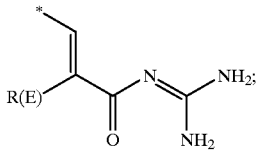

L-z is

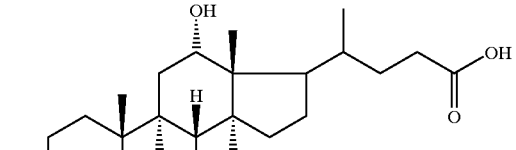

L is
—C≡C—, —NH—$CH_2$—$CH_2$—O—;

R(E) is hydrogen, $(C_1-C_4)$-alkyl;

R(1), R(2) independently of one another are hydrogen, F, Cl, CN, —$SO_2$—$CH_3$, —$(C_1-C_4)$-alkyl, —O—$(C_1-C_4)$-alkyl, where each alkyl radical is unsubstituted or substituted one or more times by F;

and their pharmaceutically tolerable salts.

"*" in the above formulae marks the point of linkage of T1 or T2 to the phenyl ring of the formula I.

If the compounds of the formula I contain one or more centers of asymmetry, these can have either the S or R configuration. The compounds can be present as optical isomers, as diastereomers, as racemates or as mixtures thereof.

The double bond geometry of the compounds of the formula I can be either E or Z. The compounds can be present in the mixture as double bond isomers.

The expression "where the alkyl radical can be substituted one or more times by F" also includes perfluorinated alkyl radicals. The designated alkyl radicals can be either straight-chain or branched.

On account of their relatively high water solubility, pharmaceutically tolerable salts are particularly suitable for medicinal applications compared with the starting or basic compounds. These salts must have a pharmaceutically tolerable anion or cation. Suitable pharmaceutically tolerable acid addition salts of the compounds according to the invention are salts of inorganic acids, such as hydrochloric acid, hydrobromic, phosphoric, metaphosphoric, nitric, sulfonic and sulfuric acid and also organic acids, such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acid. The chlorine salt is particularly preferably used for medicinal purposes. Suitable pharmaceutically tolerable basic salts are ammonium salts, alkali metal salts (such as sodium and potassium salts) and alkaline earth metal salts (such as magnesium and calcium salts).

Salts that comprise an anion which is not pharmaceutically tolerable likewise are included in the scope of the invention as useful intermediates for the preparation or purification of pharmaceutically tolerable salts and/or for use in nontherapeutic, (for example in-vitro), applications.

The term "physiologically functional derivative" used here indicates any physiologically tolerable derivative of a compound of the formula I according to the invention, e.g. an ester which on administration to a mammal, such as, for example, man, is able (directly or indirectly) to form a compound of the formula I or an active metabolite thereof.

The physiologically functional derivatives also include prodrugs of the compounds according to the invention. Such prodrugs can be metabolized in vivo to a compound according to the invention. These prodrugs can themselves be active or inactive.

A compound according to one embodiment of the invention can be present in alternative polymorphic forms, e.g. as amorphous and crystalline polymorphic forms. All polymorphic forms of the compounds according to the invention are included in the scope of the invention and are a further aspect of the invention.

Below, all references to "compound(s) according to formula (I)" relate to (a) compound(s) of the formula (I) as described above, and its/their salts, solvates and physiologically functional derivatives as described herein.

The amount of a compound according to formula (I) which is necessary in order to achieve the desired biological effect is dependent on a number of factors, e.g. the specific compound chosen, the intended use, the manner of administration and the clinical condition of the patient.

In general, a preferred daily dose lies in the range from 0.1 mg to 100 mg (typically from 0.1 mg to 50 mg) per day per kilogram of body weight, e.g. 0.1–10 mg/kg/day. Tablets or capsules can contain, for example, from 0.01 to 100 mg, typically from 0.02 to 50 mg. In the case of pharmaceutically tolerable salts, the abovementioned weight data relate to the weight of the aminopropanol ion derived from the salt. For the prophylaxis or therapy of the abovementioned conditions, the compounds according to formula (I) can be used themselves as the compound, but preferably they are present in the form of a pharmaceutical composition with a tolerable excipient. The excipient must naturally be tolerable, in the sense that it is compatible with the other constituents of the composition and is not harmful to the health of the patient. The excipient can be a solid or a liquid or both and is preferably formulated with the compound as an individual dose, for example as a tablet which can contain from 0.05% to 95% by weight of the active compound. Further pharmaceutically active substances can likewise be present, including further compounds according to formula (I). The pharmaceutical compositions according to the invention can be prepared according to one of the known pharmaceutical methods, which essentially consist in mixing the constituents with pharmacologically tolerable excipients and/or auxiliaries.

Pharmaceutical compositions according to the invention are those which are suitable for oral and peroral (e.g. sublingual) administration, although the most suitable manner of administration in each individual case is dependent on the nature and severity of the condition to be treated and on the type of compound according to formula (I) used in each case. Coated formulations and coated delayed-release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets, which in each case contain a certain amount of the compound according to formula (1), as powders or granules, as a solution or suspension in an aqueous or nonaqueous liquid, or as an oil-in-water or water-in-oil emulsion. As already mentioned, these compositions can be prepared by any suitable pharmaceutical method which includes a step in which the active compound and the excipient (which can consist of one or more additional constituents) are brought into contact. In general, the compositions are prepared by even and homogeneous mixing of the active compound with a liquid and/or finely divided solid excipient, after which the product, if necessary, is shaped. Thus a tablet, for example, can be prepared by compressing or shaping a powder or granules of the compound, if appropriate with one or more additional constituents. Pressed tablets can be produced by tableting the compound in free-flowing form, such as, for example, a powder or granules, if appropriate mixed with a binder, lubricant, inert diluent and/or a (a number of) surface-active/dispersing agent(s), in a suitable machine. Shaped tablets can be produced by shaping the pulverulent compound moistened with an inert liquid diluent in a suitable machine.

Pharmaceutical compositions which are suitable for peroral (sublingual) administration include lozenges which contain a compound according to formula (I) with a flavoring, customarily sucrose, and gum arabic or tragacanth, and pastilles which include the compound in an inert base such as gelatin and glycerol or sucrose and gum arabic.

The invention furthermore relates to a process for the preparation of a compound of the formula I, which comprises reacting a compound of the formula II $$T_1 \underset{T_2}{\overset{R_1 \quad R_2}{\diagup\!\!\!\diagdown}} G \quad + \quad A\text{—}L\text{-}z \quad \xrightarrow{\text{-GA}}$$

II

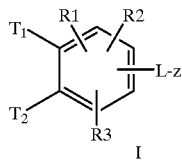

where T1, T2, R(1), R(2) and R(3) have the meaning indicated above and G is a functionality which is not replaced or replaced by L-z, with a compound A-L-z in a manner known to the person skilled in the art, GA being removed and a compound of the formula I resulting.

The functionality G of a compound of formula II can have, for example, the meaning of bromine or iodine. By means of Pd(0) catalysis, the desired C—C bond linkage can then be obtained in a known manner.

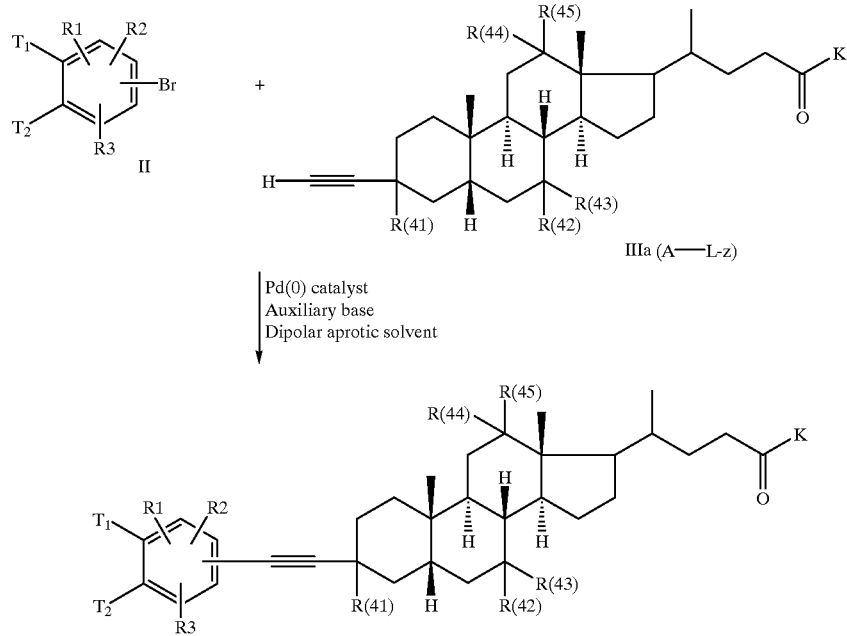

The acetylene bile acid derivatives of the formula III are prepared from suitable bile acid ketones. For this, lithium acetylide is added to keto bile acids analogously to known processes (U.S. Pat. No. 5,641,767).

Compounds of formula I and their pharmaceutically tolerable salts and physiologically functional derivatives are distinguished by a favorable influence on bile composition and prevent the formation of gallstones by preventing the supersaturation of the bile with cholesterol, or by preventing gallstone formation by delaying the formation of cholesterol crystals from supersaturated bile. The compounds can be employed on their own or in combination with lipid-lowering active compounds. The compounds are particularly suitable for the prophylaxis and treatment of gallstones.

Compounds of the formula (I) according to one embodiment of the invention pass into the hepatobiliary system and therefore act in these tissues. Thus water absorption from the gall bladder is inhibited by inhibition of the apical NHE antiport of the subtype 3 of the gall bladder epithelium, which results in a diluted bile.

Biological testing of compounds according to the invention was carried out by determining inhibition of the sodium/proton exchanger subtype 3 as described below.

1. Test Description

For the determination of $IC_{50}$ values for the inhibition of human NHE-3 protein (expressed in an LAP1 cell line), recovery of intracellular pH ($pH_i$) after acidification was determined, which commences in functional NHE even under bicarbonate-free conditions. For this study $pH_i$ was determined using the pH-sensitive fluorescent dye BCECF (Calbiochem, the precursor BCECF-AM is employed). The cells were first loaded with BCECF. BCECF fluorescence was determined in a ratio fluorescence spectrometer (Photon Technology International, South Brunswick, N.J., U.S.A.) at excitation wavelengths of 505 and 440 nm and an emission wavelength of 535 nm, and converted into $pH_i$ by use of calibration curves. The cells had already been incubated in $NH_4Cl$ buffer (pH 7.4) during the BCECF loading ($NH_4Cl$ buffer: 115 mM NaCl, 20 mM $NH_4Cl$, 5 mM KCl, 1 mM $CaCl_2$, 1 mM, $MgSO_4$ 20 mM Hepes, 5 mM glucose, 1 mg/ml BSA; a pH of 7.4 is established using 1 M NaOH).

Intracellular acidification was induced by addition of 975 $\mu l$ of an $NH_4Cl$-free buffer to 25 $\mu l$ aliquots of the cells incubated in $NH_4Cl$ buffer. The subsequent rate of pH recovery was recorded for 3 minutes. For the calculation of the inhibitory potency of the tested substances, cells were first investigated in buffers wherein a complete pH recovery or no pH recovery at all took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 is established using 1 M NaOH). For determination of 0% value, cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, pH adjusted to 7.0 with 1 M NaOH). The substances to be tested were prepared in the $Na^+$-containing buffer. The recovery of intracellular pH at each tested concentration of a substance was expressed as percent of maximum recovery. The $IC_{50}$ value of the respective substance was calculated from the percentage values of the pH recovery by means of the program SigmaPlot (Version 3.0, Jandel Scientific, U.S.A.).

Results

IC$_{50}$=1.7 μM/l         Example 1

The following examples illustrate the invention in greater detail, without restricting it to products and embodiments described in the examples.

EXAMPLES

For the convenience of the reader, the following abbreviations are used:

| | |
|---|---|
| MeOH | methanol |
| LAH | lithium aluminum hydride |
| DMF | N,N-dimethylformamide |
| EI | electron impact |
| CI | chemical ionization |
| RT | room temperature |
| EA | ethyl acetate (EtOAc) |
| mp | melting point |
| HEP | n-heptane |
| DME | dimethoxyethane |
| ES | electron spray |
| FAB | fast atom bombardment |
| CH$_2$Cl$_2$ | dichloromethane |
| THF | tetrahydrofuran |
| eq. | equivalent |

For the examples, the following method was used to couple aryl halides and substituted, terminal acetylenes:

The aryl halide (1 eq) is introduced into DMF together with an auxiliary base (4 eq) such as, for example, triethylamine and a Pd catalyst such as, for example, palladium bistriphenylphosphinodichloride (3 mol %). In the course of 0.5–3 h, the acetylene derivative is slowly added and, if necessary, the above amount of catalyst is again added. In the course of this, the reaction temperature can exceed RT and reach approximately 100° C.; it is typically 60° C. The crude product can be precipitated by addition of ethyl acetate and then filtered. Subsequent salt formation is achieved by addition of acid in acetone.

Example 1

4-{3β-[3,4-Bis(3-guanidino-2-methyl-3-oxopropenyl)phenylethynyl]-3α,7α,12α-trihydroxy-10β,13β-dimethylhexadecahydrocyclopenta[a]phenanthren-17-yl}pentanoic acid diacetate, yellowish solid, m.p. 250° C. (dec.), MS: M$^+$+H (FAB)=880

Preparation of the Intermediates 1 and 2
Intermediate 1:3β-acetylenecholic Acid

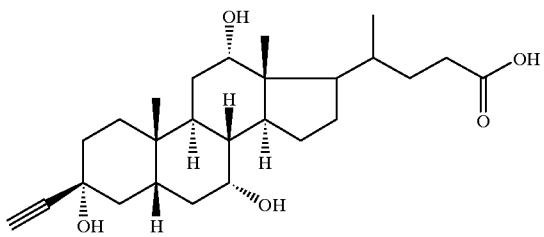

Synthesis Route a) Methyl 3,7,12-triacetylcholate 90 g of methyl cholate and 3.0 g of dimethylaminopyridine were dissolved in 500 ml of pyridine, and the solution was treated with 500 ml of acetic anhydride and stirred overnight at room temperature. It was poured onto ice water and extracted with ethyl acetate (3×). Drying (MgSO$_4$) and evaporation of the organic phase afforded 92 g of methyl 3,7,12-triacetylcholate, MS: M$^+$+Li (FAB)=555.

b) Methyl 7,12-diacetylcholate 150 ml of acetic anhydride were slowly added dropwise at 5° C. to 1.5 l of methanol. After 15 minutes, 92 g of methyl 3,7,12-triacetylcholate were added and the mixture was stirred at room temperature for 1 h. It was poured onto ice water and extracted with ethyl acetate (3×). The organic phase was washed with 1N Na$_2$CO$_3$ solution, dried using MgSO$_4$ and evaporated. 85 g of crude product were obtained, MS: M$^+$+Li (FAB)=513.

c) Methyl 3-keto-7,12-diacetylcholate 85 g (168 mmol) of methyl 7,12-diacetylcholate, 183.7 g of pyridinium chlorochromate and 175 g of molecular sieve were stirred at room temperature for 2 h in 2.5 l of dichloromethane. The mixture was poured onto 7 l of diethyl ether and the solids were filtered off. The solvent was evaporated and the residue was dissolved in ethyl acetate. After chromatography on a Florisil column, 59.6 g of product were obtained, MS: M$^+$+Li (FAB)=511.

d) Methyl 3β-acetylene-7,12-diacetylcholate

Acetylene was passed into 750 ml of abs. tetrahydrofuran at –55° C. for 25 min under argon. 145 ml of 15% n-butyllithium in hexane were added dropwise to this solution and it was stirred for 10 min. 45 g (89 mmol) of methyl 3-keto-7,12-diacetylcholate were then added and the mix-

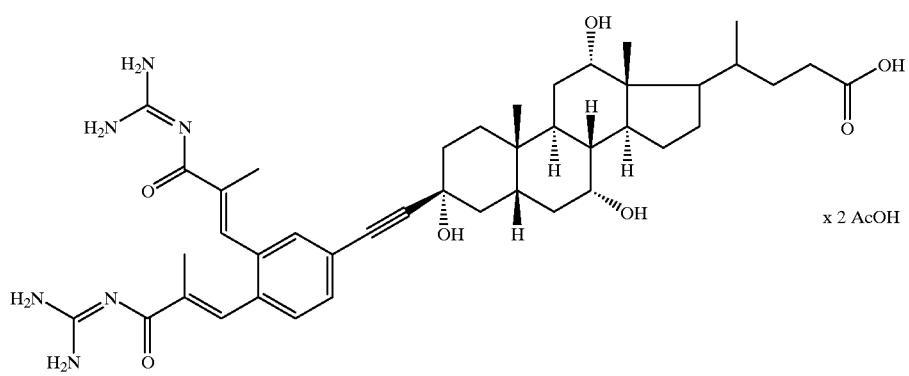

ture was stirred at −40° C. for 1.5 h. For working up, 500 ml of saturated aqueous ammonium chloride solution were added and the mixture was extracted with ethyl acetate (3×), and the organic phase was dried over MgSO$_4$ and evaporated. The residue was chromatographed on silica gel (n-heptane/ethyl acetate 1:1). 35.3 g of product were obtained, MS: M$^+$+Li (FAB)=537.

e) 3β-Acetylenecholic acid 35.2 g (66 mmol) of the product from d) were dissolved in 1 l of methanol, treated with 300 ml of 2N sodium hydroxide solution and heated under reflux for 25 h. The solvent was evaporated, the residue was dissolved in water and the solution was acidified to pH 2 using 2N hydrochloric acid. The precipitate was filtered off and washed with water until neutral. Drying of the residue afforded 14.6 g of product, MS: M$^+$+Li (FAB)=439.

Intermediate 2: 1,2-Bis[3-(E-2-methylpropenoic acid guanidide)]-4-bromobenzene dihydrochloride

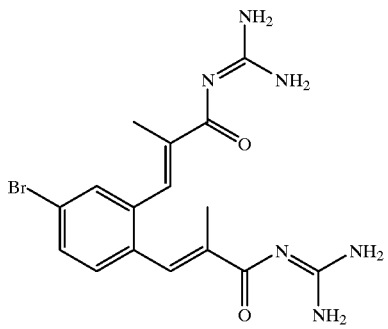

Synthesis Route a) 4-Bromo-1,2-phthalyl alcohol from dimethyl 4-bromophthalate according to standard methods (e.g. reduction with LAH), colorless oil; MS (CI): M$^+$+H=217.

b) 4-Bromo-1,2-phthalaldehyde from 2a) by, for example, Swern oxidation under standard conditions, amorphous solid, MS (CI): M$^+$+H=213.

c) 4-Bromo-1,2-di[3-(ethyl E-2-methylpropenoate)] benzene by deprotonation of 1 eq. of triethyl 2-phosphonopropionate with 1 eq. of n-butyllithium in hexane at 0° C. and subsequent reaction at RT with 0.5 eq. of 4-bromo-1,2-phthalaldehyde 2b). After complete reaction of the dialdehyde, the mixture was worked up with water and extracted three times by shaking with toluene. After drying the combined organic phases over magnesium sulfate, the solvent was removed in vacuo and the residual crude product was separated by chromatography on silica gel using EA/HEP mixtures as the eluent, colorless oil; MS (CI): M$^+$+H=381.

d) 4-Bromo-1,2-di[3-(E-2-methylpropenoic acid)] benzene from 2c) by hydrolysis according to a standard method (sodium hydroxide in methanol), colorless amorphous solid, MS (ES): M$^+$+H=325.

e) 1,2-Bis[3-(E-2-methylpropenoic acid guanidide)]-4-bromobenzene dihydrochloride from 2d) according to the general variant, colorless solid; mp 240° C.; MS (FAB): M$^+$+H=407.

f) 4-{3β-[3,4-Bis(3-guanidino-2-methyl-3-oxopropenyl) phenylethynyl]-3α,7α,12α-trihydroxy-10β,13β-dimethylhexadecahydrocyclopenta[a]phenanthren-17-yl}pentanoic acid diacetate from 2e) and 3β-acetylenecholic acid by means of Pd(0) coupling according to the general process in DMF at 60° C. in the course of 2 h.

Example 2

Benzyl 4-{3β-[3,4-bis(3-guanidino-2-methyl-3-oxopropenyl)phenylethynyl]-3α,7α,12α-trihydroxy-10β,13β-dimethylhexadecahydrocyclopenta[a] phenanthren-17-yl}pentanoate, yellowish solid, m.p. 155° C., MS: M$^+$+H (ES)=849

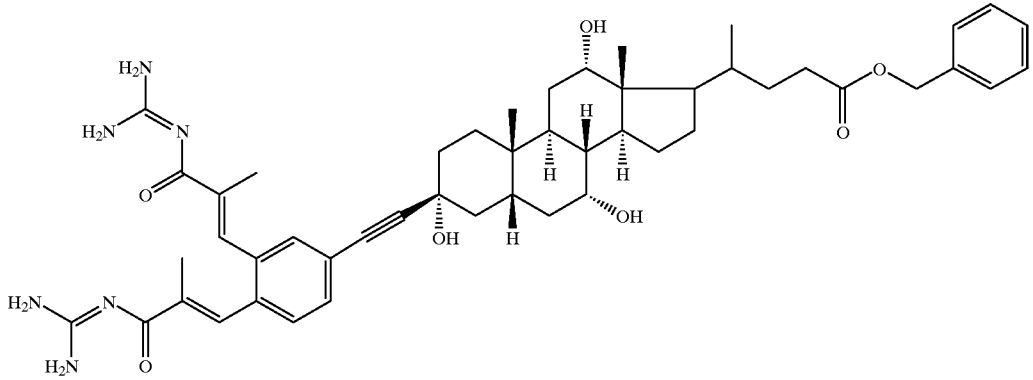

Synthesis analogously to Example 1 using benzyl 3β-acetylenecholate.

Example 3

Benzyl 4-{3β-[4-(3-guanidino-3-oxopropenyl) phenylethynyl]-3α,7α,12α-trihydroxy-10β,13β-dimethylhexadecahydrocyclopenta[a]phenanthren-17-yl}pentanoate, yellowish solid, m.p. 189° C., MS: M$^+$+H (FAB)=710

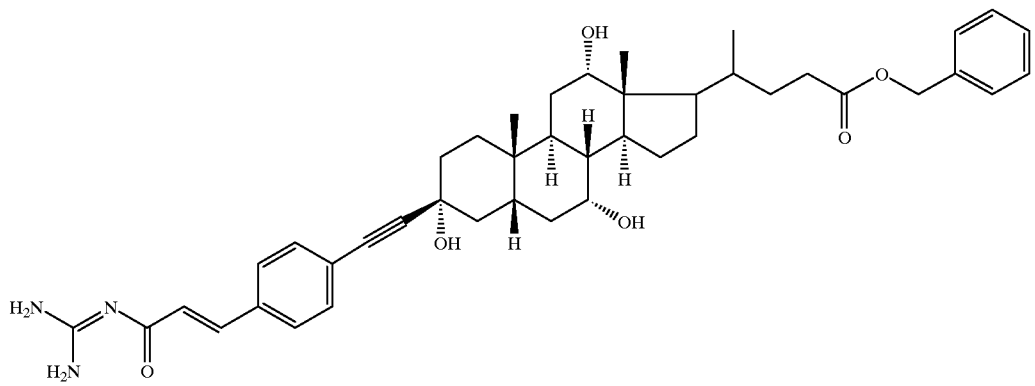

Synthesis according to the general process using 4-bromocinnamic acid guanidide and benzyl 3β-acetylenecholate.

Example 4

Methyl 4-{3β-[4-(3-guanidino-3-oxopropenyl)phenylethynyl]-3α,7α,12α-trihydroxy-10β,13β-dimethylhexadecahydrocyclopenta[a]phenanthren-17-yl}pentanoate, yellowish solid, m.p. 60° C., MS: M$^+$+H (FAB)=718

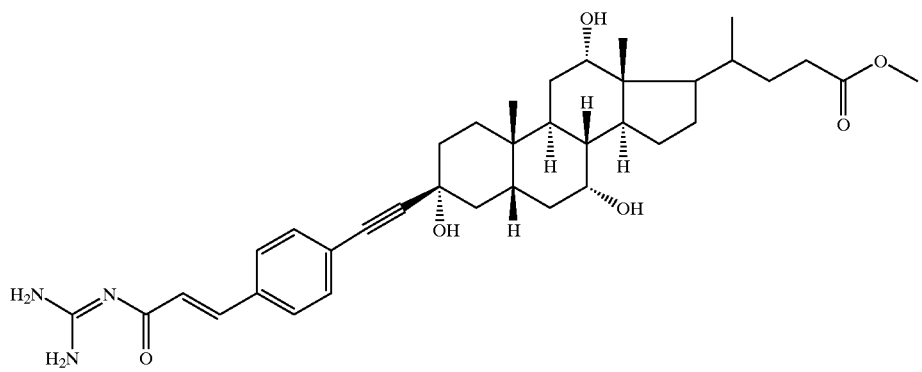

Synthesis analogously to the general process by reaction of 4-bromocinnamic acid guanidide and benzyl 3β-acetylenecholate.

Example 5

(4-{3β-[3,4-Bis(3-guanidino-2-methyl-3-oxopropenyl)phenylethynyl]-3α,7α,12α-trihydroxy-10β,13β-dimethylhexadecahydrocyclopenta[a]phenanthren-17-yl}pentanoylamino)acetic acid

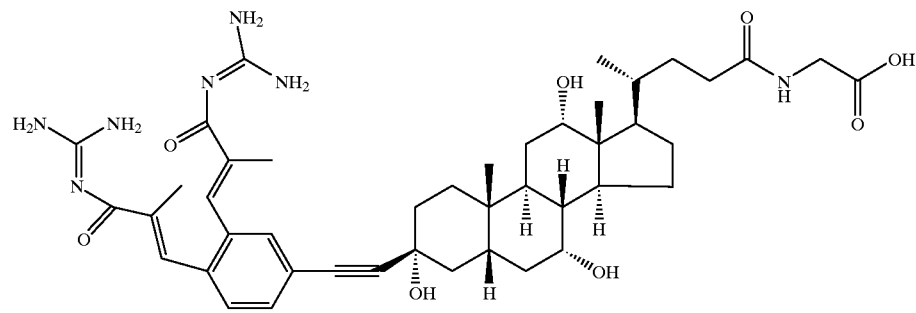

a) Methyl [4-(3β-ethynyl-3α,7α,12α-trihydroxy-10β, 13β-dimethylhexadecahydrocyclopenta[a]phenanthren-17-yl)pentanoylamino]acetate 530 mg of 3β-acetylenecholic acid (intermediate 1e) and 510 μl of triethylamine are dissolved in 30 ml of THF and 175 μl of ethyl chloroformate are added dropwise at 0° C. The mixture is stirred at 0° C. for 15 minutes, then a solution of 340 mg of glycine methyl ester hydrochloride in 10 ml of DMF is added dropwise and the mixture is stirred at RT for 4 h. It is diluted with 200 ml of EA and washed twice with 50 ml of a 5% aqueous NaHSO₄ solution each time. It is dried over MgSO₄ and the solvent is removed in vacuo. The residue is taken up in 100 ml of EA and washed 3 times with 50 ml of a saturated aqueous Na₂CO₃ solution each time. It is dried over MgSO₄ and the solvent is removed in vacuo. Chromatography on silica gel using EA/MeOH 10:1 and subsequently a second time with EA yields 280 mg of a colorless foam. R$_f$(EA)=0.37 MS (FAB): 518 (M+H)⁺ b) [4-(3β-Ethynyl-3α,7α,12α-trihydroxy-10β,13β-dimethylhexadecahydrocyclopenta[a]phenanthren-17-yl)pentanoylamino]acetic acid 270 mg of methyl [4-(3β-ethynyl-3α,7α,12α-trihydroxy-10β,13β-dimethyl-hexadecahydrocyclopenta[a]phenanthren-17-yl)pentanoylamino]acetate and 630 μl of a 1N aqueous NaOH solution are dissolved in 5 ml of ethanol and allowed to stand at RT for 16 h. The solvent is removed in vacuo, the residue is taken up using 50 ml of a saturated aqueous NaH₂PO₄ solution and the mixture is extracted 3 times with 50 ml of EA each time. It is dried over MgSO₄ and the solvent is removed in vacuo. 230 mg of an amorphous solid are obtained. R$_f$(acetone/water 10:1)=0.25 MS (FAB): 502 (M+2Li)⁺ c) (4-{3β-[3,4-Bis(3-guanidino-2-methyl-3-oxopropenyl)phenylethynyl]-3α,7α,12α-trihydroxy-10β,13β-dimethylhexadecahydrocyclopenta[a]phenanthren-17-yl}pentanoylamino)acetic acid 230 mg of [4-(3β-ethynyl-3α,7α,12α-trihydroxy-10β, 13β-dimethylhexadecahydrocyclopenta[a]phenanthren-17-yl)pentanoylamino]acetic acid and 183 mg of N-{3-[4-bromo-2-(3-guanidino-2-methyl-3-oxopropenyl)phenyl]-2-methylacryloyl}guanidine are reacted at 60° C. in the course of 3 h by means of Pd(0) coupling according to the general process. After preparative HPLC on C18 LiChrosorb using acetonitrile/water 2:4+0.1% acetic acid +0.1% ammonium acetate, 70 mg of an amorphous solid are obtained. R$_f$(n-butanol/glacial acetic acid/water 3:1:1)=0.33 MS (ES): 816 (M+H)⁺

Example 6

4-{3-[2-Fluoro-4-(3-guanidino-2-methyl-3-oxopropenyl)phenylethynyl]-3,7,12-trihydroxy-10,13-dimethylhexadecahydrocyclopenta[a]phenanthren-17-yl}pentanoic acid a) Butyl 3-(4-bromo-3-fluorophenyl)-2-methylacrylate 2 g of 1-bromo-2-fluoro-4-iodobenzene and 1.1 ml of diisoproplethylamine are dissolved in 20 ml of dimethylacetamide (anhydrous) and a gentle stream of argon is passed through the solution for 5 minutes. 1.4 ml of butyl acrylate and 10 mg of 2,6-di-t-butyl-4-methylphenol are then added and the mixture is heated to 100° C. Finally, a further 4 ml of dimethylacetamide are degassed by means of a stream of argon and 80 mg of trans-bis(O-acetato)bis[o-(di-o-tolylphosphino)benzyl]dipalladium (Tetrahedron Lett. 1996, 37(36), 6535–6538) are suspended therein. This suspension is added to the mixture of the other reactants and stirred at 140° C. for 90 minutes. The mixture is then diluted with 200 ml of EA and washed twice with 100 ml of water each time and once with 100 ml of a saturated aqueous NaCl solution. It is dried over MgSO₄ and the solvent is removed in vacuo. Chromatography on silica gel yields 230 mg of a colorless oil. R$_f$(EA/HEP)=0.27 MS (DCI): 315 (M+H)⁺ b) Butyl 3-{4-[17-(3-carboxy-1-methylpropyl)-3,7,12-trihydroxy-10,13-dimethylhexadecahydrocyclopenta[a]phenanthren-3-ylethynyl]-3-fluorophenyl}-2-methylacrylate 64 mg of bis(triphenylphosphine)palladium(II) chloride, 17 mg of CuI, 0.5 ml of triethylamine and 230 mg of butyl 3-(4-bromo-3-fluorophenyl)-2-methylacrylate are dissolved in 10 ml of anhydrous DMF and a solution of 395 mg of 3β-acetylenecholic acid in 10 ml of anhydrous DMF is added dropwise at 60° C. in the course of one hour. The mixture is stirred at 60° C. for one hour and then a solution of 395 mg of 3β-acetylenecholic acid in 10 ml of anhydrous DMF is slowly added dropwise again at 60° C. The mixture is stirred at 60° C. for a further 2 hours, then 64 mg of bis(triphenylphosphine)palladium(II) chloride and 17 mg of CuI are added once more and the mixture is again stirred at 60° C. for 2 hours. Finally, a further 80 mg of 3β-acetylenecholic acid are added and the mixture is stirred at 60° C. for 2 hours. The solvent is removed in vacuo and the residue is taken up in 100 ml of a 5% aqueous NaHSO₄ solution and extracted 3 times with 100 ml of EA each time. It is dried over Na₂SO₄ and the solvent is removed in vacuo. Chromatography on silica gel using EA/MeOH 5:1 yields 90 mg of a wax-like substance. R$_f$(EA/MeOH 5:1)=0.56 MS (FAB): 667 (M+H)⁺ c) 4-{3-[2-Fluoro-4-(3-guanidino-2-methyl-3-oxopropenyl)phenylethynyl]-3,7,12-trihydroxy-10,13-dimethylhexadecahydrocyclopenta[a]phenanthren-17-yl}pentanoic acid 73 mg of guanidine hydrochloride and 71 mg of potassium t-butoxide are dissolved in 2 ml of anhydrous DMF and the mixture is stirred at RT for 30 minutes. This suspension is injected into 85 mg of butyl 3-{4-[17-(3-carboxy-1-methylpropyl)-3,7,12-trihydroxy-10,13-dimethylhexadecahydrocyclopenta[a]phenanthren-3-ylethynyl]-3-fluorophenyl}-2-methylacrylate and the

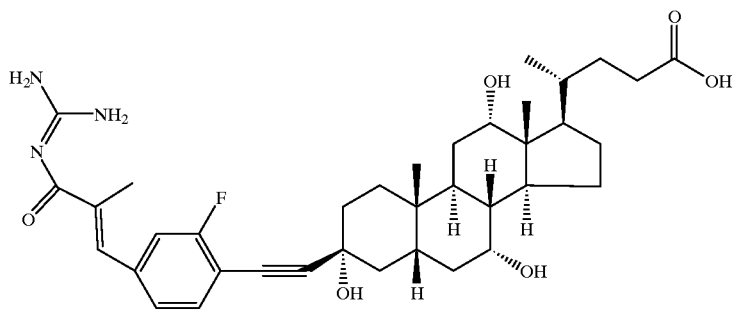

mixture is stirred at 100° C. for 5 hours. After cooling, 10 ml of water are added, and the mixture is adjusted to pH=4 using aqueous HCl solution and extracted 3 times with 10 ml of EA each time. The organic phase is dried over MgSO₄ and the solvent is removed in vacuo. Chromatography on silica gel using acetone/water 10:1 yields 15.5 mg of an amorphous solid. R_f(acetone/water 10:1)=0.19 MS (ES): 652 (M+H)⁺

Example 7

4-(3-{2-[2,6-Difluoro-4-(3-guanidino-2-methyl-3-oxopropenyl)phenylamino]ethoxy}-7,12-dihydroxy-10,13-dimethylhexadecahydrocyclopenta[a]phenanthren-17-yl)-pentanoic acid

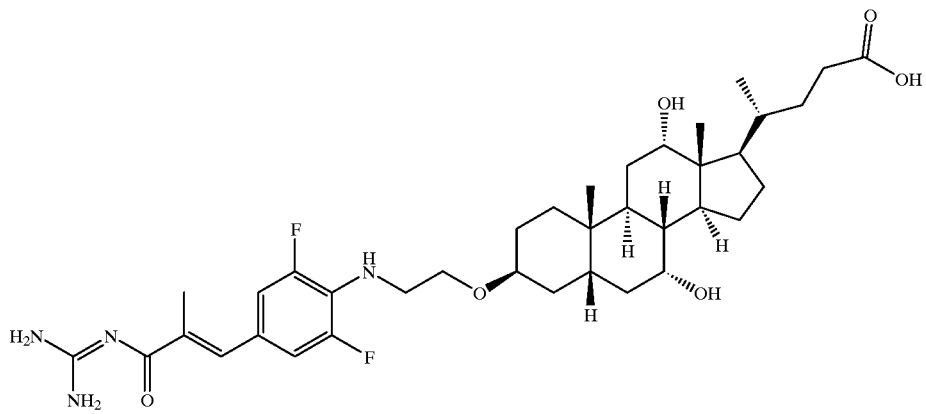

a) 4-(7,12-Dihydroxy-3-methanesulfonyloxy-10,13-dimethylhexadecahydrocyclopenta[a]phenanthren-17-yl) pentanoic acid 100 g of cholic acid are dissolved in 500 ml of pyridine and 23.1 ml of mesyl chloride are added dropwise at 0° C. over a period of 30 minutes. The mixture is stirred at RT for 3 hours, then poured onto a solution of 400 ml of H₂SO₄ in 3 l of water at 0° C. and extracted 4 times with 750 ml of EA each time. The organic phase is dried over Na₂SO₄ and the solvent is removed in vacuo. The residue is crystallized using diisopropyl ether and 117.1 g are obtained; m.p. 121° C. (with decomposition). R_f(EA/HEP/acetic acid 5:5:1)= 0.31 MS (FAB): 487 (M+H)⁺ b) Methyl 4-[7,12-Dihydroxy-3-(2-hydroxyethoxy)-10, 13-dimethylhexadecahydrocyclopenta[a]phenanthren-17-yl]pentanoate 116 g of 4-(7,12-dihydroxy-3-methanesulfonyloxy-10,13-dimethylhexadecahydrocyclopenta[a]phenanthren-17-yl) pentanoic acid and 130 ml of triethylamine are dissolved in 650 ml of glycol and the mixture is stirred at 100° C. for 3 hours and at 115° C. for 7.5 hours. The reaction mixture is poured onto a solution of 400 ml of H₂SO₄ in 3 l of water at 0° C. and extracted 7 times with 750 ml of EA each time. The organic phase is dried over Na₂SO₄ and the solvent is removed in vacuo. The intermediate ZWP is obtained.

130 ml of acetyl chloride are added dropwise at 0° C. to 900 ml of methanol. A solution of ZWP in 400 ml [lacuna] is then added and the mixture is stirred at RT for 6 hours. It is allowed to stand at RT for 60 hours, then poured onto 2.6 l of water and extracted 8 times with 500 ml of diisopropyl ether (DIP) each time. The organic phase is then washed 6 times with 600 ml of a half-saturated aqueous NaHCO₃ solution each time. It is dried over Na₂SO₄ and the solvent is removed in vacuo. Chromatography on silica gel using EA yields 32 g of a resin-like solid. R_f(EA)=0.19 MS (FAB): 467 (M+H)⁺ c) Methyl 4-{3-[2-(1,3-dioxo-1,3-dihydroisoindol-2-yl)ethoxy]-7,12-dihydroxy-10,13-dimethylhexadecahydrocyclopenta[a]phenanthren-17-yl}pentanoate 1.5 g of methyl 4-[7,12-dihydroxy-3-(2-hydroxyethoxy)-10,13-dimethylhexadecahydrocyclopenta[a]phenanthren-17-yl]pentanoate, 950 mg of triphenylphosphine and 550 mg of phthalimide are heated at 45° C. in 26 ml of THF and 1.14 ml of diethyl azodicarboxylate are added dropwise at this temperature. The reaction mixture is stirred at 45° C. for 2 hours, then poured into 200 ml of a half-concentrated aqueous NaHCO₃ solution and extracted 3 times with 200 ml of EA each time. The organic phase is dried over Na₂SO₄ and the solvent is removed in vacuo. Chromatography on silica gel using t-butyl methyl ether (MTB) yields 1.76 g of a viscous oil. R_f(EA)=0.60 MS (FAB): 602 (M+Li)⁺ d) Methyl 4-[3-(2-aminoethoxy)-7,12-dihydroxy-10,13-dimethyl-hexadecahydrocyclopenta[a]phenanthren-17-yl]-pentanoate 1.7 g of methyl 4-{3-[2-(1,3-dioxo-1,3-dihydroisoindol-2-yl)ethoxy]-7,12-dihydroxy-10,13-dimethylhexadecahydrocyclopenta[a]phenanthren-17-yl}pentanoate and 0.52 ml of hydrazine hydrate (80%) are dissolved in 14 ml of methanol and the solution is refluxed for 3 hours. It is then cooled to 40° C. and the reaction mixture is treated with 8.7 ml of a 2N aqueous HCl solution. It is stirred at 40° C. for 30 minutes, then the volatile constituents are removed in vacuo. Chromatography on silica gel using acetone/water 10:1 yields 540 mg of resin-like solid. R_f(acetone/water 10:1)=0.06 MS (FAB): 466 (M+H)⁺ e) 4-[3-(2-Aminoethoxy)-7,12-dihydroxy-10,13-dimethylhexadecahydrocyclopenta[a]phenanthren-17-yl] pentanoic acid 3 g of methyl 4-[3-(2-aminoethoxy)-7,12-dihydroxy-10, 13-dimethylhexadecahydrocyclopenta[a]phenanthren-17-yl]pentanoate and 310 mg of NaOH are stirred at RT for 24 hours in 5 ml of water and 30 ml of methanol. The solvents are removed in vacuo, the residue is taken up with 200 ml of water and the mixture is adjusted to pH=7–7.5 using aqueous HCl solution. It is stirred for 1 hour and the product is then filtered off. 1.6 g of a pale yellow crystalline solid, m.p. 185–195° C., are obtained. R_f(CH₂Cl₂/MeOH/acetic acid/water 32:8:1:1)=0.18 MS (ES): 452 (M+H)⁺ f) Ethyl 2-methyl-3-(3,4,5-trifluorophenyl)acrylate 4.3 ml of triethyl 2-phosphonopropionate are dissolved in 30 ml of anhydrous THF and 12.5 ml of a 1.6N solution of n-butyllithium in hexane are added dropwise at 0° C. The mixture is stirred at RT for 15 minutes and a solution of 3.2 g of 3,4,5-trifluorobenzaldehyde in 8 ml of anhydrous THF is then added dropwise. The mixture is stirred at RT for one hour and allowed to stand at RT for 16 hours. The reaction mixture is diluted with 300 ml of water, 30 ml of a saturated aqueous $Na_2CO_3$ solution are added and it is extracted 3 times with 100 ml of EA each time. The organic phase is dried over $Na_2SO_4$ and the solvent is removed in vacuo. Chromatography on silica gel using EA/HEP 1:8 yields 3.8 g of colorless crystals; m.p. 54° C. $R_f$(EA/HEP 1:8)=0.35 MS (DCI): 245 $(M+H)^+$ g) Ethyl 3-(4-{2-[17-(3-carboxy-1-methylpropyl)-7,12-dihydroxy-10,13-dimethylhexadecahydrocyclopenta[a]phenanthren-3-yloxy]ethylamino}-3,5-difluorophenyl)-2-methylacrylate 600 mg of 4-[3-(2-aminoethoxy)-7,12-dihydroxy-10,13-dimethylhexadecahydrocyclopenta[a]phenanthren-17-yl]pentanoic acid, 390 mg of ethyl 2-methyl-3-(3,4,5-trifluorophenyl)acrylate and 828 mg of $K_2CO_3$ are stirred at 130° C. for 2.5 hours in 10 ml of dimethylacetamide. After cooling, the reaction mixture is diluted with 400 ml of $CH_2Cl_2$ and washed with 400 ml of a 5% aqueous $NaHSO_4$ solution. It is dried over $MgSO_4$ and the solvent is removed in vacuo. Chromatography on silica gel using $CH_2Cl_2$/MeOH 10:1 yields 155 mg of a colorless oil. $R_f$($CH_2Cl_2$/MeOH 10:1)=0.27 MS (ES): 676 $(M+H)^+$ i) 4-(3-{2-[2,6-Difluoro-4-(3-guanidino-2-methyl-3-oxopropenyl)phenylamino]ethoxy}-7,12-dihydroxy-10,13-dimethylhexadecahydrocyclopenta[a]phenanthren-17-yl) pentanoic acid 130 mg of guanidine hydrochloride and 125 mg of potassium t-butoxide are stirred at RT for 30 minutes in 1 ml of anhydrous DMF. A solution of 150 mg of ethyl 3-(4-{2-[17-(3-carboxy-1-methylpropyl)-7,12-dihydroxy-10,13-dimethylhexadecahydrocyclopenta[a]phenanthren-3-yloxy]ethylamino}-3,5 -difluorophenyl)-2-methylacrylate in 1 ml of anhydrous DMF is then added and the mixture is stirred at 110–115° C. for 6 hours. The reaction mixture is then poured onto 100 ml of water, adjusted to pH=6 using aqueous HCl solution and the product is filtered off. It is dried in a fine vacuum and 8.0 mg of an amorphous solid are obtained. $R_f$($CH_2C_{12}$/MeOH/acetic acid/water 32:8:1:1)= 0.21 MS (ES): 689 $(M+H)^+$ All documents cited herein are specifically incorporated by reference in their entireties. Priority document 19849722.9 (Federal Republic of Germany) filed Oct. 28, 1998 specifically is incorporated by reference in its entirety.

We claim:

1. A compound described by formula I

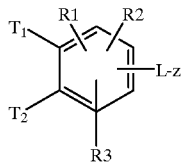

I wherein one of T1 and T2 is

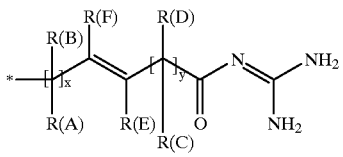

and the other one of T1 and T2 is hydrogen or each of T1 and T2 is

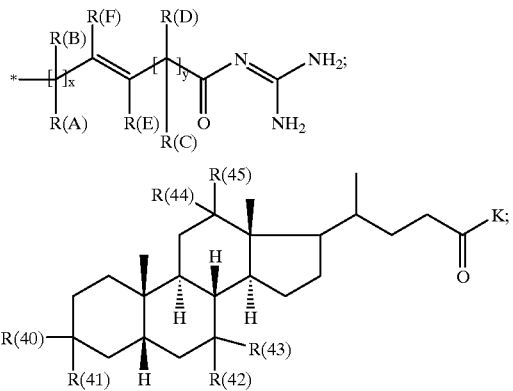

R(A), R(B), R(C), R(D) independently of one another are selected from the group consisting of hydrogen, F, Cl, Br, I, CN, OH, $NH_2$, —($C_1$–$C_8$)-alkyl, and —O—($C_1$–$C_8$)-alkyl, wherein each alkyl radical is unsubstituted or is substituted at least once with a substituent selected from the group consisting of F; ($C_3$–$C_8$)-cycloalkyl, phenyl, benzyl, NHR(7), NR(7)R(8), O—($C_3$–$C_6$)-alkenyl, O—($C_3$–$C_8$)-cycloalkyl, O-phenyl, and O-benzyl, wherein the phenyl nucleus is unsubstituted or is substituted 1 to 3 times by a substituent selected from the group consisting of F, Cl, $CF_3$, methyl, methoxy, and NR(9)R(10);

R(7), R(8) independently of one another are selected from the group consisting of hydrogen, —($C_1$–$C_8$)-alkyl, and a chain of 4 or 5 methylene groups formed from both R(7) and R(8) wherein one $CH_2$ group is not replaced or replaced by oxygen, sulfur, NH, N—$CH_3$ or N-benzyl, and wherein the alkyl radical is unsubstituted or is substituted at least once by a substituent selected from the group consisting of F, ($C_3$–$C_8$)-cycloalkyl, ($C_3$–$C_6$)-alkenyl, ($C_3$–$C_8$)-cycloalkyl, phenyl, and benzyl, wherein the phenyl nucleus is unsubstituted or is substituted 1 to 3 times by a substituent selected from the group consisting of F, Cl, $CF_3$, methyl, methoxy, and NR(9)R(10);

R(9), R(10) independently of one another are selected from the group consisting of hydrogen, ($C_1$–$C_4$)-alkyl, and ($C_1$–$C_4$)-perfluoroalkyl;

x is zero, 1 or 2;

y is zero, 1 or 2;

R(E), R(F) independently of one another are selected from the group consisting of hydrogen, F, Cl, Br, I, CN, ($C_1$–$C_8$)-alkyl, and O—($C_1$–$C_8$)-alkyl, wherein each alkyl radical is unsubstituted or is substituted at least once by a substituent selected from the group consisting of F, ($C_3$–$C_8$)-cycloalkyl, O—($C_3$–$C_6$)-alkenyl, O—($C_3$–$C_8$)-cycloalkyl, O-phenyl, and O-benzyl, wherein the phenyl nucleus is unsubstituted or is substituted 1 to 3 times by a substituent selected from the group consisting of F, Cl, $CF_3$, methyl, methoxy, and NR(9)R(10);

R(1), R(2), R(3) independently of one another are selected from the group consisting of hydrogen, F, Cl, Br, I, CN, —($C_1$–$C_8$)-alkyl, and —O—($C_1$–$C_8$)-alkyl, wherein each alkyl radical is unsubstituted or is substituted at least once by a substituent selected from the group consisting of F, —(C=O)—N=C($NH_2$)$_2$, —($SO_{0-2}$)—($C_1$–$C_8$)-alkyl, —($SO_2$)—NR(7)R(), —O—($C_0$–$C_8$)-alkylenephenyl, and —($C_0$–$C_8$)-alkylenephenyl, wherein each phenyl nuclei is unsubstituted or is substituted 1 to 3 times by a substituent selected from the group consisting of F, Cl, $CF_3$, methyl, methoxy, and —($C_0$–$C_8$)-alkylene-NR(9)R(10);

L is —O—, —NR(47)-, —($C_1$–$C_8$)-alkylene-, —($C_1$–$C_8$)-alkenylene-, —($C_1$–$C_8$)-alkynylene-, —COO—, —CO—NR(47)-, —$SO_2$—NR(47)-, —O—($CH_2$)$_n$—O—, —NR(47)-($CH_2$)$_n$—O—, —NR(48)-CO—($CH_2$)$_n$—O—, —CO—NR(48)-($CH_2$)$_n$—O—, —O—CO—($CH_2$)$_n$—O—, —$SO_2$—NR(48)-($CH_2$)$_n$—O—, —NR(48)-CO—$CH_2$—$CH_2$—CO—NR(48)-($CH_2$)$_n$—O—, —NR(48)-CO—CH=CH—CO—NR(48)-($CH_2$)$_n$—O—, or —NR(48)-$SO_2$—($CH_2$)$_n$—O—;

R(47) is hydrogen, ($C_1$–$C_8$)-alkyl, R(48)-CO—, phenyl, or benzyl;

R(48) is hydrogen, ($C_1$–$C_8$)-alkyl, phenyl or benzyl, wherein the phenyl nucleus is unsubstituted or is substituted 1 to 3 times by a substituent selected from the group consisting of F, Cl, $CF_3$, methyl, and methoxy;

n is 1, 2, 3, 4, 5, 6, 7, or 8;

R(40) to R(45) independently of one another are selected from the group consisting of hydrogen, —OR(50), —SR(50), NHR(50), —NR(50)$_2$, —O—(CO)—R(50), —S—(CO)—R(50), —NH—(CO)—R(50), —O—PO—(OR(50))—OR(50), —O—($SO_2$)—OR(50), —R(50) and a bond to L; or R(40) and R(41), R(42) and R(43), R(44) and R(45) in each case together form an oxygen of a carbonyl group, and wherein only one of the radicals R(40) to R(45) forms a bond with L;

K is —OR(50), —NHR(50), —NR(50)$_2$, —HN—$CH_2$—$CH_2$—$CO_2$H, —HN—$CH_2$—$CH_2$—$SO_3$H, —NH—$CH_2$—COOH, —N($CH_3$)$CH_2$$CO_2$H, —HN—CH(R46)$CO_2$H, or —OKa, wherein Ka is an ion selected from the group consisting of a cation, an alkali metal cation, an alkaline earth metal cation and a quaternary ammonium ion;

R(46) is ($C_1$–$C_4$)-alkyl, benzyl, —$CH_2$—OH, $H_3$CS$CH_2$$CH_2$—, HO$_2$CC$H_2$, or HO$_2$CC$H_2$$CH_2$—;

R(50) is hydrogen, ($C_1$–$C_4$)-alkyl, phenyl or benzyl, wherein the phenyl nucleus is unsubstituted or is substituted 1 to 3 times by a substituent selected from the group consisting of F, Cl, $CF_3$, methyl, and methoxy;

a pharmaceutically tolerable salt of the compound of formula I.

2. A compound as described in claim 1, wherein one of T1 and T2 is

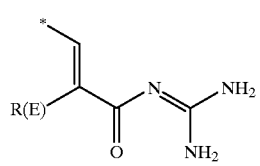

and the other one of T1 and T2 is hydrogen or each of T1 and T2 is

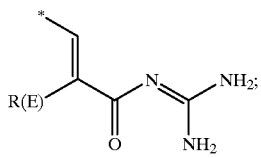

L-z is

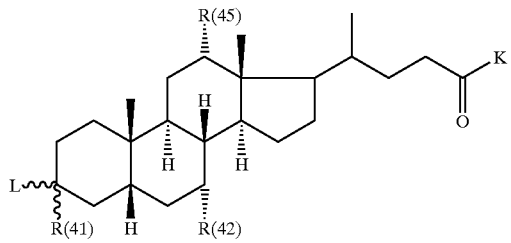

R(E) is hydrogen, F, Cl, CN, ($C_1$–$C_4$)-alkyl, or —O—($C_1$–$C_4$)-alkyl, wherein the alkyl radical is unsubstituted or is substituted at least once by a substituent selected from the group consisting of F, ($C_3$–$C_6$)-cycloalkyl, ($C_3$–$C_8$)-alkenyl, O—($C_3$–$C_6$)-cycloalkyl, O-phenyl, and O-benzyl, wherein the phenyl nucleus is unsubstituted or is substituted 1 to 3 times by a substituent selected from the group consisting of F, Cl, $CF_3$, methyl, methoxy, and NR(9)R(10);

R(9), R(10) are selected from the group consisting of hydrogen, $CH_3$, and $CF_3$;

R(1), R(2), R(3) are selected from the group consisting of hydrogen, F, Cl, CN, —$SO_2$—($C_1$–$C_4$)-alkyl, —$SO_2$—N(($C_1$–$C_4$)-alkyl)$_2$, —$SO_2$—NH($C_1$–$C_4$)-alkyl, —$SO_2$—$NH_2$, —$SO_2$—($C_1$–$C_4$)-alkyl, —($C_1$–$C_4$)-alkyl, and —O—($C_1$–$C_4$)-alkyl, wherein each alkyl radical is unsubstituted or is substituted at least once by a substituent selected from the group consisting of F, —O—($C_0$–$C_4$)-alkylenephenyl, and —($C_0$–$C_4$)-alkylenephenyl, wherein the phenyl nucleus is unsubstituted or is substituted 1 to 3 times by a substituent selected from the group consisting of F, Cl, $CF_3$, methyl, and methoxy;

L is —O—, —NR(47)-, —($C_1$–$C_4$)-alkylene-, —($C_1$–$C_4$)-alkenylene-, —($C_1$–$C_4$)-alkynylene-, —COO—, —CO—NR(47)-, —$SO_2$—NR(47)-, —O—($CH_2$)$_n$—O—, —NR(47)-($CH_2$)$_n$—O—, —NR(48)-CO—($CH_2$)$_n$—O—, —CO—NR(48)-($CH_2$)$_n$—O—, or —$SO_2$—NR(48)-($CH_2$)$_n$—O—;

R(47) is hydrogen, ($C_1$–$C_4$)-alkyl, R(48)-CO—, or phenyl, benzyl;

R(48) is hydrogen, ($C_1$–$C_4$)-alkyl, phenyl or benzyl, wherein the phenyl nucleus is unsubstituted or is substituted 1 to 3 times by a substituent selected from the group consisting of F, Cl, $CF_3$, methyl, and methoxy;

n is between 1 and 4;

R(41), R(42), R(45) independently of one another are selected from the group consisting of hydrogen, —OR(50), NHR(50), —NR(50)$_2$, —O—(CO)—R(50), and —NH—(CO)—R(50);

R(50) is hydrogen, ($C_1$–$C_4$)-alkyl, phenyl or benzyl, wherein the phenyl nucleus is unsubstituted or is substituted 1 to 3 times by a substituent selected from the group consisting of F, Cl, $CF_3$, methyl, and methoxy;

K is —OR(50), —NHR(50), —NR(50)$_2$, —HN—$CH_2$—$CH_2$—$CO_2$H, —HN—$CH_2$—$CH_2$—$SO_3$H, —NH—$CH_2$—COOH, —N($CH_3$)$CH_2$$CO_2$H, or —OKa, wherein Ka is an selected from the group consisting of a cation, an alkali metal ion, an alkaline earth metal ion and a quaternary ammonium ion;

a pharmaceutically tolerable salt of the compound of formula I.

3. A compound as described in claim 1, wherein one of T1 and T2 is

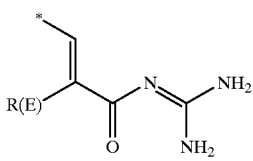

and the other one of T1 or T2 is hydrogen or each of T1 and T2 is

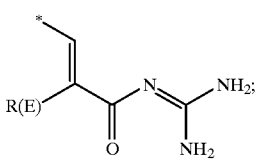

L-z is

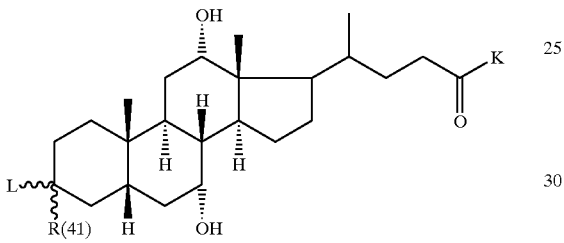

R(E) is hydrogen, F, Cl, CN, $(C_1-C_4)$-alkyl, $(C_1-C_4)$-alkyl, —O$(C_1-C_4)$-alkyl, $CF_3$, or —OCF$_3$;

R(1), R(2) independently of one another are selected from the group consisting of hydrogen, F, Cl, CN, —SO$_2$—CH$_3$, SO$_2$NH$_2$—, —(C$_1$–C$_4$)-alkyl, and —O—(C$_1$–C$_4$)-alkyl, wherein each alkyl radical is unsubstituted or is substituted at least once by F; —O—(C$_0$–C$_4$)-alkylenephenyl, or —(C$_0$–C$_4$)-alkylenephenyl, wherein each phenyl nucleus is unsubstituted or is substituted 1 to 3 times by a substituent selected from the group consisting of F, Cl, CF$_3$, methyl, and methoxy;

R(3) is hydrogen;

L is —O—, —NR(47)-, —CH$_2$—CH$_2$—, CH=CH—, —(C≡C)—, —COO—, —CO—NR(47)-, —SO$_2$—NR(47)-, —O—(CH$_2$)$_n$—O—, —NR(47)-(CH$_2$)$_n$—O—, —NR(48)-CO—(CH$_2$)$_n$—O—, —CO—NR(48)-(CH$_2$)$_n$—O—, or —SO$_2$—NR(48)-(CH$_2$)$_n$—O—;

R(47) is hydrogen, (C$_1$–C$_4$)-alkyl, R(48)-CO—, phenyl, or benzyl;

R(48) is hydrogen, (C$_1$–C$_4$)-alkyl, phenyl or benzyl, wherein the phenyl nucleus is unsubstituted or is substituted 1 to 3 times by a substituent selected from the group consisting of F, Cl, CF$_3$, methyl, and methoxy;

n is between 1 and 4;

R(41) is hydrogen, or —OH;

K is —OR(50), —NHR(50), —NR(50)$_2$, —HN—CH$_2$—CH$_2$—CO$_2$H, —HN—CH$_2$—CH$_2$—SO$_3$H, —NH—CH$_2$—COOH, —N(CH$_3$)CH$_2$CO$_2$H, —OKa, where Ka is a cation;

R(50) is hydrogen, (C$_1$–C$_4$)-alkyl, phenyl or benzyl, where the phenyl nucleus is unsubstituted or substituted 1 to 3 times by F, Cl, CF$_3$, methyl, methoxy;

or its pharmaceutically tolerable salts.

4. A compound as described in claim 1, wherein the compound further is described by formula Ia.

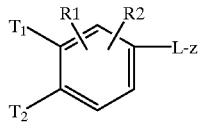

wherein

R3 is H;

one of T1 and T2 is

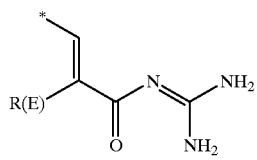

and the other one of T1 and T2 is hydrogen or each of T1 and T2 is

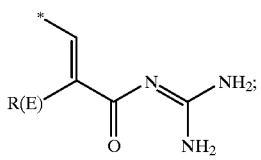

L-z is

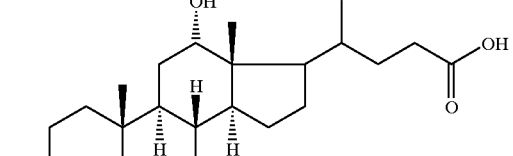

L is

—C≡C—   or   —NH—CH$_2$—CH$_2$—O—;

R(E) is hydrogen, or (C$_1$–C$_4$)-alkyl;

R(1), R(2) independently of one another are selected from the group consisting of hydrogen, F, Cl, CN, —SO$_2$—CH$_3$, —(C$_1$–C$_4$)-alkyl, and —O—(C$_1$–C$_4$)-alkyl, wherein each alkyl radical is unsubstituted or is substituted at least once by F;

or a pharmaceutically tolerable salt thereof.

5. A pharmaceutical composition comprising at least one compound as described in claim 1 and an excipient.

6. A pharmaceutical composition as claimed in claim 5 further comprising at least one additional lipid-lowering active compound.

7. A method for the prophylaxis or treatment of gallstones comprising administering a composition that comprises a compound as claimed in claim 1 to a patient in need thereof.

8. A method as described in claim 7 wherein the composition further comprises at least one additional lipid-lowering active compound.

9. A process for the production of a pharmaceutical composition that comprises at least one compound as described in claim 1, comprising the step of mixing the compound with a pharmaceutically suitable excipient in a form suitable for administration to a patient.

10. A pharmaceutical composition comprising at least one compound as described in claim 2 and an excipient.

11. A pharmaceutical composition as claimed in claim 10 further comprising at least one additional lipid-lowering active compound.

12. A method for the prophylaxis or treatment of gallstones comprising administering a composition that comprises a compound as claimed in claim 2 to a patient in need thereof.

13. A process for the production of a pharmaceutical composition that comprises at least one compound as described in claim 2, comprising the step of mixing the compound with a pharmaceutically suitable excipient in a form suitable for administration to a patient.

14. A pharmaceutical composition comprising at least one compound as described in claim 3 and an excipient.

15. A pharmaceutical composition as claimed in claim 14 further comprising at least one additional lipid-lowering active compound.

16. A method for the prophylaxis or treatment of gallstones comprising administering a composition that comprises a compound as claimed in claim 3 to a patient in need thereof.

17. A process for the production of a pharmaceutical composition that comprises at least one compound as described in claim 3, comprising the step of mixing the compound with a pharmaceutically suitable excipient in a form suitable for administration to a patient.

18. A pharmaceutical composition comprising at least one compound as described in claim 4 and an excipient.

19. A pharmaceutical composition as claimed in claim 18 further comprising at least one additional lipid-lowering active compound.

20. A method for the prophylaxis or treatment of gallstones comprising administering a composition that comprises a compound as claimed in claim 4 to a patient in need thereof.

* * * * *